US009523686B2

(12) United States Patent
Raychaudhuri et al.

(10) Patent No.: US 9,523,686 B2
(45) Date of Patent: Dec. 20, 2016

(54) METHODS AND MATERIALS FOR THE DETECTION OF DENGUE VIRUS INFECTION

(71) Applicant: Inbios International, Inc., Seattle, WA (US)

(72) Inventors: Syamal Raychaudhuri, Seattle, WA (US); Raymond L. Houghton, Bothell, WA (US); Stanislaw Morkowski, Seattle, WA (US); Yvonne Stevens, Bellevue, WA (US); Mohua Bose, Redmond, WA (US); James William Needham, Seattle, WA (US); Hongjing Chen, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 37 days.

(21) Appl. No.: 14/566,321

(22) Filed: Dec. 10, 2014

(65) Prior Publication Data

US 2015/0086978 A1 Mar. 26, 2015

Related U.S. Application Data

(62) Division of application No. 13/629,445, filed on Sep. 27, 2012, now Pat. No. 8,920,804.

(60) Provisional application No. 61/579,598, filed on Dec. 22, 2011.

(51) Int. Cl.

| | |
|---|---|
| ***C07K 16/08*** | (2006.01) |
| ***G01N 33/569*** | (2006.01) |
| ***A61K 39/42*** | (2006.01) |
| ***G01N 33/543*** | (2006.01) |
| ***G01N 33/558*** | (2006.01) |
| ***C07K 16/10*** | (2006.01) |

(52) U.S. Cl.

CPC ..... *G01N 33/56983* (2013.01); *C07K 16/1081* (2013.01); *G01N 33/54366* (2013.01); *G01N 33/558* (2013.01); *C07K 2317/33* (2013.01); *G01N 2333/185* (2013.01)

(58) Field of Classification Search

None

See application file for complete search history.

(56) References Cited

U.S. PATENT DOCUMENTS

| | | | |
|---|---|---|---|
| 6,190,859 | B1 | 2/2001 | Putnak et al. |
| 6,682,883 | B1 | 1/2004 | Monath et al. |
| 6,870,032 | B1 | 3/2005 | Flamand et al. |
| 7,473,424 | B2 | 1/2009 | Burton et al. |
| 7,622,113 | B2 | 11/2009 | Lai et al. |
| 2004/0209244 | A1 | 10/2004 | Burton et al. |
| 2007/0166701 | A1 | 7/2007 | Chang |

OTHER PUBLICATIONS

Dussart, Philippe et al., "Evaluation of an Enzyme Immunoassay for Detection of Dengue Virus NS1 Antigen in Human Serum," Clinical and Vaccine Immunology, vol. 13, No. 11, pp. 1185-1189 (Nov. 2006).

Falconer, A.K.I. et al., "Production of Dimer-Specific and Dengue Virus Group Cross-Reactive Mouse Monoclonal Antibodies to the Dengue 2 Virus Non-Structural Glycoprotein NS1," Journal of General Virology, vol. 72, pp. 961-965 (1991).

Flamand, Marie et al., "Dengue Virus Type 1 Non-Structural Glycoprotein NS1 is Secreted from Mammalian Cells as a Soluble Hexamer in a Glycosylation-Dependent Fashion," Journal of Virology, vol. 73, No. 7, pp. 6104-6110 (Jul. 1999).

Kumarasamy, V. et al., "Evaluating the Sensitivity of a Commercial Dengue NS1 Antigen-Capture ELISA for Early Diagnosis of Acute Dengue Virus Invection," Singapore Medical Journal, vol. 48, No. 7, pp. 669-673 (2007).

Qiu, Li-wen et al., "Development of an Antigen Capture Immunoassay Based on Monoclonal Antibodies Specific for Dengue Virus Serotype 2 Nonstructural Protein 1 for Early and Rapid Identification of Dengue Virus Serotype 2 Infections," Clinical and Vaccine Immunology, vol. 16, No. 1, pp. 88-95 (Jan. 2009).

Young, Paul R. et al., "An Antigen Capture Enzyme-Linked Immunosorbent Assay Reveals High Levels of the Dengue Virus Protein NS1 in the Sera of Infected Patients," Journal of Clinical Microbiology, vol. 38, No. 3, pp. 1053-1057 (Mar. 2000).

*Primary Examiner* — Stacy B Chen

(57) ABSTRACT

The present invention provides monoclonal antibodies that are specific for the Dengue non-structural glycoprotein NS1 in monomeric and/or oligomeric (primarily dimeric) form, together with methods, including ELISA and lateral flow assays, that employ the disclosed antibodies for the early detection of Dengue virus infection. Diagnostic kits for the detection of Dengue infection are also provided, such kits including the disclosed monoclonal and/or polyclonal antibodies.

21 Claims, 4 Drawing Sheets

Dengue NS1 sandwich ELISA

```
SEQUENCE LISTING

<160> NUMBER OF SEQ ID NOS: 8

<210> SEQ ID NO 1
<211> LENGTH: 380
<212> TYPE: PRT
<213> ORGANISM: Dengue virus

<400> SEQUENCE: 1

Met Asn Ser Arg Ser Thr Ser Leu Ser Val Ser Leu Val Leu Val Gly
 1               5                  10                  15

Val Val Thr Leu Tyr Leu Gly Val Met Val Gln Ala Asp Ser Gly Cys
            20                  25                  30

Val Val Ser Trp Lys Asn Lys Glu Leu Lys Cys Gly Ser Gly Ile Phe
        35                  40                  45

Ile Thr Asp Asn Val His Thr Trp Thr Glu Gln Tyr Lys Phe Gln Pro
    50                  55                  60

Glu Ser Pro Ser Lys Leu Ala Ser Ala Ile Gln Lys Ala His Glu Glu
```

```
65                  70                  75                  80

Gly Ile Cys Gly Ile Arg Ser Val Thr Arg Leu Glu Asn Leu Met Trp
                85                  90                  95

Lys Gln Ile Thr Pro Glu Leu Asn His Ile Leu Ser Glu Asn Glu Val
            100                 105                 110

Lys Leu Thr Ile Met Thr Gly Asp Ile Lys Gly Ile Met Gln Ala Gly
        115                 120                 125

Lys Arg Ser Leu Gln Pro Gln Pro Thr Glu Leu Lys Tyr Ser Trp Lys
    130                 135                 140

Thr Trp Gly Lys Ala Lys Met Leu Ser Thr Glu Ser His Asn Gln Thr
145                 150                 155                 160

Phe Leu Ile Asp Gly Pro Glu Thr Ala Glu Cys Pro Asn Thr Asn Arg
                165                 170                 175

Ala Trp Asn Ser Leu Glu Val Glu Asp Tyr Gly Phe Gly Val Phe Thr
            180                 185                 190

Thr Asn Ile Trp Leu Lys Leu Arg Glu Lys Gln Asp Val Phe Cys Asp
        195                 200                 205

Ser Lys Leu Met Ser Ala Ala Ile Lys Asp Asn Arg Ala Val His Ala
    210                 215                 220

Asp Met Gly Tyr Trp Ile Glu Ser Ala Leu Asn Asp Thr Trp Lys Ile
225                 230                 235                 240

Glu Lys Ala Ser Phe Ile Glu Val Lys Ser Cys His Trp Pro Lys Ser
                245                 250                 255

His Thr Leu Trp Ser Asn Gly Val Leu Glu Ser Glu Met Ile Ile Pro
            260                 265                 270

Lys Asn Phe Ala Gly Pro Val Ser Gln His Asn Tyr Arg Pro Gly Tyr
        275                 280                 285

His Thr Gln Thr Ala Gly Pro Trp His Leu Gly Lys Leu Glu Met Asp
    290                 295                 300

Phe Asp Phe Cys Glu Gly Thr Thr Val Val Val Thr Glu Asp Cys Gly
305                 310                 315                 320

Asn Arg Gly Pro Ser Leu Arg Thr Thr Thr Ala Ser Gly Lys Leu Ile
                325                 330                 335

Thr Glu Trp Cys Cys Arg Ser Cys Thr Leu Pro Pro Leu Arg Tyr Arg
            340                 345                 350

Gly Glu Asp Gly Cys Trp Tyr Gly Met Glu Ile Arg Pro Leu Lys Glu
        355                 360                 365

Lys Glu Glu Asn Leu Val Asn Ser Leu Val Thr Ala
    370                 375                 380


<210> SEQ ID NO 2
<211> LENGTH: 118
<212> TYPE: PRT
<213> ORGANISM: Murine

<400> SEQUENCE: 2

Ile Gln Val Lys Leu Glu Glu Ser Gly Pro Gly Leu Val Lys Pro Ser
 1               5                  10                  15

Gln Ser Leu Ser Leu Thr Cys Ser Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser Tyr Ser Gly Ser Thr Arg Tyr Asn Pro Ser
    50                  55                  60
```

```
Leu Ile Ser Arg Ala Ser Ile Thr Arg Asp Thr Ser Lys Asn Gln Phe
65                  70                  75                  80

Phe Leu Leu Leu Asn Ser Val Thr Thr Glu Asp Thr Ala Thr Tyr Tyr
                85                  90                  95

Cys Ala Arg Ser Pro Ile Tyr Ser Phe Asp Tyr Trp Gly Gln Gly Thr
            100                 105                 110

Thr Leu Thr Val Ser Ser
        115


<210> SEQ ID NO 3
<211> LENGTH: 110
<212> TYPE: PRT
<213> ORGANISM: Murine

<400> SEQUENCE: 3

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Ser Leu Ala Ser Ser Leu Glu Ser Gly Val Pro Ala
    50                  55                  60

Arg Phe Ser Gly Gly Gly Ser Gly Thr Asp Phe Thr Leu Asn Ile His
65                  70                  75                  80

Pro Val Glu Glu Asp Asp Ala Ala Thr Tyr Tyr Cys Gln His Ser Arg
                85                  90                  95

Asp Leu Pro Thr Phe Gly Gly Gly Thr Lys Leu Glu Ile Lys
            100                 105                 110


<210> SEQ ID NO 4
<211> LENGTH: 121
<212> TYPE: PRT
<213> ORGANISM: Murine

<400> SEQUENCE: 4

Gln Val Gln Leu Gln Gln Ser Gly Gly Asp Leu Val Lys Pro Gly Gly
 1               5                  10                  15

Ser Leu Arg Leu Ser Cys Ala Ala Ser Gly Phe Ser Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ile Ser Thr Phe Tyr Pro Asp Ser Val
    50                  55                  60

Lys Gly Arg Phe Thr Ile Ser Lys Asp Asn Ala Lys Asn Thr Leu Tyr
65                  70                  75                  80

Leu Gln Met Ser Gly Leu Lys Ser Asp Asp Thr Ala Met Tyr Tyr Cys
                85                  90                  95

Ala Arg His Gly Ala Tyr Tyr Arg Pro Ala Trp Phe Ala Tyr Trp Gly
            100                 105                 110

Gln Gly Thr Leu Val Thr Val Ser Ala
        115                 120


<210> SEQ ID NO 5
<211> LENGTH: 112
<212> TYPE: PRT
<213> ORGANISM: Murine
```

```
<400> SEQUENCE: 5

Asp Ile Val Leu Thr Gln Ser Thr Ser Ser Leu Ala Val Ser Ala Gly
 1               5                  10                  15

Glu Lys Val Thr Met Arg Cys Lys Ser Ser Gln Ser Val Leu Ser Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Trp Thr Phe Gly Gly Gly Thr Lys Leu Glu Ile Lys
            100                 105                 110


<210> SEQ ID NO 6
<211> LENGTH: 117
<212> TYPE: PRT
<213> ORGANISM: Murine

<400> SEQUENCE: 6

Gln Val Gln Leu Gln Gly Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asn Pro Asn Asn Gly Arg Ile Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Phe Tyr Tyr Phe Gly Pro Arg Trp Gly Gln Gly Thr Leu
            100                 105                 110

Val Thr Val Ser Ala
        115


<210> SEQ ID NO 7
<211> LENGTH: 107
<212> TYPE: PRT
<213> ORGANISM: Murine

<400> SEQUENCE: 7

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
```

-continued

```
                85                  90                  95

Thr Phe Gly Gly Gly Thr Lys Leu Glu Ile Lys
            100                 105


<210> SEQ ID NO 8
<211> LENGTH: 118
<212> TYPE: PRT
<213> ORGANISM: Murine

<400> SEQUENCE: 8

Ser Gln Val Gln Leu Gln Gln Pro Gly Ala Glu Leu Val Lys Pro Gly
 1               5                  10                  15

Ala Ser Val Lys Leu Ser Cys Lys Ala Ser Gly Tyr Thr Phe Thr Ser
            20                  25                  30

Tyr Trp Met Gln Trp Val Lys Gln Arg Pro Gly Gln Gly Leu Glu Trp
        35                  40                  45

Ile Gly Glu Ile Asn Pro Asn Asn Gly Arg Ile Asn Tyr Asn Glu Lys
    50                  55                  60

Phe Lys Asn Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Asp Phe Tyr Tyr Phe Gly Pro Arg Trp Gly Gln Gly Thr
            100                 105                 110

Leu Val Thr Val Ser Ala
        115
```

METHODS AND MATERIALS FOR THE DETECTION OF DENGUE VIRUS INFECTION

REFERENCE TO PRIORITY APPLICATIONS

This application is a divisional application of U.S. patent application Ser. No. 13/629,445, filed Sep. 27, 2012, now U.S. Pat. No. 8,920,804 which claims priority to U.S. Provisional Patent Application No. 61/579,598 filed Dec. 22, 2011. These patent applications are incorporated herein by reference in their entireties.

STATEMENT REGARDING FEDERALLY SPONSORED RESEARCH OR DEVELOPMENT

This invention was made with government support under grant numbers 1R43AI074172-01 and 5R43AI074172-02 awarded by the National Institutes of Health. The government has certain rights in the invention.

FIELD OF THE INVENTION

The present invention relates generally to the diagnosis of dengue virus infection. More specifically, the invention relates to the immunological detection of dengue fever using monoclonal antibodies raised against the dengue glycoprotein NS1.

BACKGROUND OF THE INVENTION

Dengue fever is one of most threatening mosquito-borne viral diseases in humans. It is caused by four closely related virus serotypes (DEN1, DEN2, DEN3 and DEN4) of the *flavivirus* genus within the Flaviviridae family. The dengue virus is transmitted by mosquitoes of the *Aedes* genus (particularly *Aedes aegypti*) and causes a febrile illness in tropical and sub-tropical regions. More than two billion inhabitants live in endemic regions and are at risk of dengue virus infection. According to the World Health Organization (WHO), the incidence of dengue infection increased 30-fold over the last 50 years (Dussart et al., Clin. Vaccine Immunol., 2006, 13:1185-1189), and is responsible for an estimated 50-100 million new infections annually, as well as 500,000 hospitalizations and 30,000 deaths, mostly in children.

Clinical signs of dengue infection usually appear five to eight days after infection and are characterized by undifferentiated fever (referred to as dengue fever), accompanied by severe headaches, lumbago, muscle and joint pain, and shivering. From the third to the fifth day of the febrile phase, a congestive maculopapular rash may appear (referred to as conventional dengue). In the majority of cases, disease usually subsides within a week. However, in the severe form, the infection can progress to hemorrhagic syndrome (referred to as dengue hemorrhagic fever) and fatal hypovolemic shock (referred to as dengue shock syndrome), which has a high mortality rate.

All four dengue serotypes are able to cause clinical symptoms of dengue infection, which provides a life-long immunity to the homologous dengue serotype, but does not protect against heterologous dengue serotype. Therefore, any person in an endemic area is susceptible to four infections during their lifetime. Secondary infection with a heterologous serotype may lead to more severe manifestations of disease, probably due to complement activation by antigen-antibody complexes (Young et al., J. Clin. Microbiol., 2000, 38:1053-1057; Xu et al., J. Clin. Microbiol., 2006, 44:2872-2878).

During the replication of dengue virus, a non-structural glycoprotein, NS1, associates with the membrane on the cell surface and is released into the circulation as early as 1 day post-onset of symptoms (Xu et al., 2006, Ibid). The early expression of the NS1 protein makes it a good diagnostic target for an early dengue infection as antibody-based diagnostic assays are capable of detecting dengue-specific antibody production later in the course of the infection (7-10 days post infection).

The mature dengue NS1 protein contains 352 amino acid residues in a base polypeptide of ~40 kDa, with glycosylation increasing the apparent mass of the protein on SDS-PAGE (Flamand et al., J. Virol., 1999, 73:6104-6110). The protein includes twelve invariant cysteine residues and two N-glycosylation sites (at N130 and N207) conserved among all flavivirus NS1 proteins, indicating their importance to the structure and function of the protein.

NS1 exists in both intracellular and extracellular forms. Immature NS1 exists as a hydrophilic monomer in the endoplasmic reticulum lumen, and is rapidly processed into a stable hydrophobic non-covalent homodimer, with the subunits interacting via their carboxyl termini (Flamand et al., 1999, Ibid). Upon dimerization, NS1 becomes associated with intracellular membrane components. The ability to form intracellular dimers appears to be particularly important for trafficking and secretion from the cell. In mammalian cells, NS1 is secreted from infected cells into the extracellular milieu, either as a soluble protein, which may be present in a higher oligomeric form than a dimer, or in association with microparticles but not with virions. Studies have identified NS1 soluble tetramers and soluble, detergent-labile, hexamers (Wallis et al., J. Biol. Chem., 2004, 279: 20729-20741; and Flamand et al., 1999, Ibid). It has been postulated that the glycosylation status of NS1 determines the oligomeric distribution of secreted NS1. Even though the role of NS1 glycoprotein is not clearly defined, some studies have indicated that intracellular NS1 glycoprotein may be indirectly involved in viral replication, with extracellular NS1 glycoprotein being involved in the formation of immunogenic complexes and triggering complement mediated immune response, resulting in a more severe form of illness.

Currently, there is no commercially available vaccine for dengue virus. In the absence of immunization, the monitoring of dengue virus outbreaks and serological mapping of new outbreaks become critically important to the control and containment of infection. As clinical manifestations for dengue virus infections are quite unspecific, it is difficult to affirm diagnosis without laboratory testing. Programs have been set up by WHO to actively monitor vector insects and cases of fever, as well as to perform serological and virological screening of individuals suspected of being infected with dengue virus. Thus, the development of diagnostic assays for dengue infection is critically important.

Early diagnosis is essential for proper timely treatment of the patient. The currently available tests for dengue include RT-PCR for viral RNA and immunologic tests for dengue-specific antibody or viral proteins. However, many of these tests have significant disadvantages. For example, RT-PCR for viral RNA requires expensive laboratory equipment and trained personnel, which makes it hard to use on a large scale or in rural areas. Some dengue-specific enzyme linked immunosorbent assays (ELISAs) can detect IgM or IgG that appear later during the course of infection, however diagnosis as early as day two of infection is preferable (Alcon et al., J. Clin. Microbiol., 2002, 40:376-381).

A comparative analysis of four diagnostic methods for dengue infection, namely virus isolation, viral RNA detection, dengue specific IgM detection and NS1 antigen detection, revealed that NS1 antigen detection had the highest sensitivity rate compared to the other three methods (Kumarasamy et al., Singapore Med. J., 2007, 48:669-673). Several immunological tests employing specific peptides (including NS1) derived from dengue virus have been proposed. U.S. Pat. Nos. 7,282,341, 6,870,032, 5,824,506, 6,682,883, 6,190,859 and PCT Patent Publication WO99/009414 describe methods of using peptides as a diagnostic tool for determining the presence of dengue virus.

Alcon et al. (J. Clin. Microbiol., 2002, 40:376-381) have described an ELISA for NS1 detection and demonstrated that NS1 is present at high levels in patient sera during primary and secondary infection. NS1 is detectable during the whole clinical phase of illness and can be detected in the first few days of infection (as early as the first day of fever). Falconar and Young have described the production of dimer-specific and dengue virus group cross-reactive mouse monoclonal antibodies to dengue 2 virus NS1 (J. Gen. Virol., 1991, 72:961-965), and the use of certain of these antibodies in an ELISA for NS1 has been described (Young et al., J. Clin. Microbiol., 2000, 38:1053-1057). High levels of NS1 were found in acute phase sera, but not in convalescent phase sera, from some of the patients with serologically confirmed dengue 2 virus secondary infection.

U.S. Pat. No. 6,870,032 describes a method for detecting NS1 protein in the hexameric form, and the selection of antibodies specific for NS1 protein in hexameric form, together with the use of such antibodies in the early detection of flavivirus infection. All these studies demonstrate that antibodies directed to different epitopes of NS1 and NS1 oligomeric forms, as well as NS1-immune complexes, may play different roles in the diagnosis of dengue virus infection.

SUMMARY

Dengue virus NS1 is a versatile protein that exists in various forms. Recent reports have demonstrated that dengue virus NS1 can be expressed as a dimer and monomer in addition to oligomeric and hexameric configurations (Somnuke et al., Virology, 2011, 413(2):253-64). U.S. Pat. No. 6,870,032 discloses a NS1 detection assay based on recognition of a hexamer form of the NS1 molecule. Herein we describe a set of antibody reagents specific for dengue NS1 that recognize monomeric, dimeric and also possibly multimeric, forms of the mammalian expressed NS1.

The present disclosure provides monoclonal and polyclonal antibodies, and antigen binding fragments thereof, that are specific for monomeric and oligomeric (primarily dimeric) forms of the dengue virus NS1 polypeptide, together with methods for the use of such antibodies in the diagnosis of dengue virus infection, and kits for use in such methods. The disclosed methods and compositions are effective in the early detection of dengue virus infection and can readily be used in the field, leading to rapid treatment and to control of disease outbreak.

In one aspect, polyclonal and monoclonal antibodies are provided that are specific for the NS1 polypeptide originating from Dengue virus 2 serotype and expressed as described in the U.S. Pat. No. 7,332,322 by Frolov et al., Feb. 19, 2008. The amino acid sequence of this polypeptide is provided in SEQ ID NO: 1. In certain embodiments, the monoclonal antibodies disclosed herein specifically bind to a non-hexameric form of NS-1. In specific embodiments, the disclosed monoclonal antibodies comprise at least one variable region selected from the group consisting of amino acid sequences provided herein as SEQ ID NO: 2-8.

In related aspects, isolated polynucleotides that encode the disclosed amino acid sequences, together with vectors comprising such polynucleotides and host cells transformed or transfected with the polynucleotides, are also provided.

In another aspect, the present disclosure provides diagnostic tests, including ELISA and lateral flow assays, employing the disclosed polyclonal and/or monoclonal antibodies that can be effectively employed to detect dengue virus infection in a subject, such as a human. Such assays can be employed to detect the presence of dengue virus infection using biological samples including blood, serum, plasma, saliva, cerebrospinal fluid, urine, and other tissue specimens (Monique da Rocha Queiroz Lima et al., PLOSNTDS, v5 (5), e1147, 2011).

In one embodiment, the disclosed assays employ a first antibody specific for dengue NS1 as a capture antibody, with a second antibody specific for dengue NS1 in monomeric and/or oligomeric (primarily dimeric) forms being employed as a detection antibody. In certain embodiments, the second antibody is specific for a non-hexameric form of NS1. Preferably, the detection antibody is labeled with a detection agent. For example, in certain embodiments, a rabbit polyclonal antibody raised against NS1 is employed as the capture antibody, and a monoclonal antibody disclosed herein is employed as the detection antibody. Alternatively, a monoclonal antibody disclosed herein can be employed as the capture antibody, with a rabbit polyclonal antibody raised against NS1 being employed as the detection antibody.

In certain embodiments, the detection reagent comprises a reporter group selected from the group consisting of: enzymes, substrates, cofactors, inhibitors, dyes, radionuclides, luminescent groups, fluorescent groups, colorimetric indicators and biotin. In the case of an ELISA, the detection antibody can be unlabeled and a goat anti-mouse IgG1 horseradish peroxidase can be employed as a separate detection reagent. Alternatively, the detection antibody can be conjugated to horseradish peroxidase prior to use in the assay. For a lateral flow assay, the detection antibody is preferably labeled with a colorimetric or fluorescent indicator, such as colloidal gold or a fluorescent dye, thereby allowing a user to determine visually whether a test is positive or negative for dengue infection.

In a related aspect, kits for the diagnosis of dengue virus infection by ELISA are provided, such kits comprising: (a) a solid surface on which a polyclonal antibody specific for the dengue NS1 polypeptide is immobilized; (b) at least one control selected from the group consisting of: positive dengue virus controls, negative dengue virus controls and cutoff controls; and (c) a solution containing at least one monoclonal antibody specific for a dengue NS1 polypeptide oligomer (primarily dimer) and/or monomer, as disclosed herein.

In a further aspect, dipsticks for use in the lateral flow assays disclosed herein are provided. In certain embodiments, such dipsticks comprise: (a) a lateral flow membrane; (b) a first area positioned at a first, lower, end of the lateral flow membrane for receiving a test sample, wherein the first area comprises a first antibody specific for a monomeric and/or oligomeric (primarily dimeric) form of the dengue NS1 polypeptide, the antibody being labeled with a reporter agent; (c) a second area positioned at a second, upper, end of the lateral flow membrane comprising an immobilized control polypeptide; and (d) a third area positioned between the first and second areas, wherein the third area comprises an immobilized second, different, antibody specific for a monomeric and/or oligomeric (primarily dimeric) form of the dengue NS1 polypeptide. In certain embodiments, the first antibody is a polyclonal antibody, and the second antibody is a monoclonal antibody disclosed herein.

Diagnostic kits comprising such dipsticks are also provided. In certain embodiments, such diagnostic kits comprise a dipstick plus at least one of the following components: a vessel containing lysing buffer; and a pipette for applying the test solution to the dipstick.

In certain embodiments, the kits disclosed herein are sealably contained within a container, such as an aluminum pouch, that is generally impermeable to gases and fluids.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION OF THE INVENTION

Figure 1:
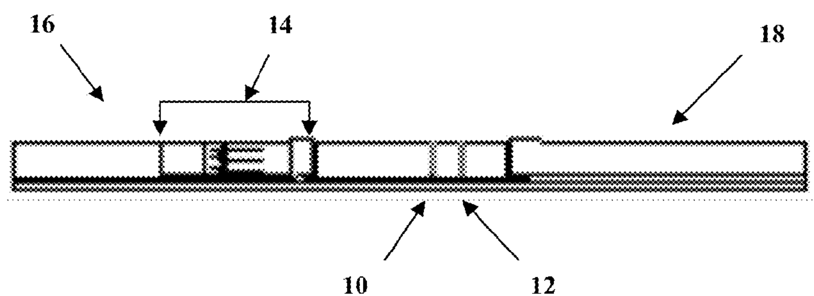
FIG. 1 shows a dipstick for use in a lateral flow assay of the present disclosure.

In one embodiment, the present invention provides methods and materials for detecting dengue virus infection in a biological sample, such as blood, serum, plasma, saliva, cerebrospinal fluid and urine, taken from individuals, such as humans and/or other mammals, suspected of being infected with dengue virus. The presence of dengue virus infection is detected using one or more of the assays described herein to determine the presence or absence of the dengue NS1 protein in a biological sample. The amino acid sequence for dengue virus NS1 is provided in SEQ ID NO: 1. In certain embodiments, the disclosed assays employ monoclonal antibodies specific for monomeric and/or oligomeric (primarily dimeric) forms of NS1. In other embodiments, the disclosed assays employ monoclonal antibodies specific for monomeric and/or oligomeric (primarily dimeric) forms of NS1 in combination with polyclonal antibodies specific for dengue virus NS1 polypeptide.

The monoclonal antibodies of the present disclosure specifically or selectively bind to a monomeric and/or oligomeric (primarily dimeric) form of the dengue NS1 polypeptide, while not significantly binding other components present in a test sample. As used herein, the term "antibodies specific for" a defined target molecule refer to antibodies that bind a target molecule with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$ or $10^{13}$ $M^{-1}$. Alternatively, binding affinity may be defined as an equilibrium dissociation constant ($K_d$) of a particular binding interaction with units of M (e.g., $10^{-5}$ M to $10^{-13}$ M). Binding affinities of antibodies can be readily determined using techniques well known to those of skill in the art (see, e.g., Scatchard et al. (1949) Ann. N.Y. Acad. Sci. 51:660; U.S. Pat. Nos. 5,283,173; 5,468,614; Biacore® analysis; or the equivalent). In certain embodiments, the polyclonal and/or monoclonal antibodies disclosed herein are preselected by immunocapture on the dengue virus NS1 glycoprotein. In specific embodiments, the antibodies disclosed herein are monoclonal antibodies having variable regions that include at least one amino acid sequence selected from the group consisting of: SEQ ID NO: 2-8.

Terms understood by those in the art as referring to antibody technology are each given the meaning acquired in the art, unless expressly defined herein. For example, the terms "$V_L$" and "$V_H$" refer to the variable binding region derived from an antibody light and heavy chain, respectively. The variable binding regions are made up of discrete, well-defined sub-regions known as "complementarity determining regions" (CDRs) and "framework regions" (FRs). The terms "$C_L$" and "$C_H$" refer to an "immunoglobulin constant region," i.e., a constant region derived from an antibody light or heavy chain, respectively, with the latter region understood to be further divisible into $C_{H1}$, $C_{H2}$, $C_{H3}$ and $C_{H4}$ constant region domains, depending on the antibody isotype (IgA, IgD, IgE, IgG, IgM) from which the region was derived. A portion of the constant region domains makes up the Fc region (the "fragment crystallizable" region), which contains domains responsible for the effector functions of an immunoglobulin, such as ADCC (antibody-dependent cell-mediated cytotoxicity), ADCP (antibody-dependent cell-mediated phagocytosis), CDC (complement-dependent cytotoxicity) and complement fixation, binding to Fc receptors, greater half-life in vivo relative to a polypeptide lacking an Fc region, and protein A binding. A polypeptide containing an Fc region allows for dimerization or multimerization of the polypeptide. A "hinge region," also referred to herein as a "linker," is an amino acid sequence interposed between and connecting the variable binding and constant regions of a single chain of an antibody, which is known in the art as providing flexibility in the form of a hinge to antibodies or antibody-like molecules. Immunoglobulin structure and function are reviewed, for example, in Harlow et al., Eds., *Antibodies: A Laboratory Manual*, Chapter 14 (Cold Spring Harbor Laboratory, Cold Spring Harbor, 1988). An extensive introduction as well as detailed information about all aspects of recombinant antibody technology can be found in the textbook *Recombinant Antibodies* (John Wiley & Sons, NY, 1999). A comprehensive collection of detailed antibody engineering laboratory protocols can be found in R. Kontermann and S. Dübel, Eds.,

*The Antibody Engineering Lab Manual* (Springer Verlag, Heidelberg/New York, 2000).

Antibodies to purified, recombinant or synthesized antigens can be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the antigen, such as NS1, may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the antigen may then be purified from such antisera by, for example, affinity chromatography using the antigen coupled to a suitable solid support.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies can be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies can then be harvested from the ascites fluid or the blood. Contaminants can be removed from the antibodies by conventional techniques, such as chromatography, gel filtration, precipitation and extraction.

There are a variety of assay formats known to those of ordinary skill in the art for using antibodies to detect an antigen in a sample which can be effectively employed in the disclosed methods. See, e.g., Harlow and Lane, *Antibodies: A Laboratory Manual*, Cold Spring Harbor Laboratory, 1988. In one such assay format, an antibody, such as a polyclonal NS1-specific antibody (referred to as the capture antibody) is immobilized on a solid support (as described below) and contacted with the sample to be tested. After removal of the unbound sample, a second monoclonal antibody or antibody mixture specific for NS1 (referred to as the detection antibody(s)), which has been labeled with a reporter group, may be added and used to detect bound antigen.

In an exemplary competitive assay, the sample is combined with either a monoclonal or polyclonal antibody against NS1, which has been labeled with a suitable reporter group. The mixture of sample and antibody is then combined with polypeptide antigen, such as NS1, immobilized on a suitable solid support. Antibody that has not bound to NS1 in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of dengue virus infection in the sample. To determine the presence or absence of dengue virus infection, the signal detected from the reporter group that remains bound to the solid support is generally compared to a signal that corresponds to a predetermined cut-off value. Such cut-off values may generally be determined as described below. Any of the reporter groups discussed below may be used to label the antibodies, and binding may be detected by any of a variety of techniques appropriate for the reporter group employed.

In one embodiment, the disclosed assay involves the use of antibody immobilized on a solid support to bind to and remove the antigen from the sample. The bound antigen may then be detected using a detection reagent that binds to the antigen/antibody complex and contains a detectable reporter group. Suitable detection reagents include antibodies that bind to the antigen/antibody complex labeled with a reporter group. Alternatively, a competitive assay may be utilized, in which an antibody that binds to the antigen is labeled with a reporter group and allowed to bind to the immobilized antigen after incubation of the antibody with the sample. The extent to which components of the sample inhibit the binding of the labeled antibody to the antigen is indicative of the reactivity of the sample with the immobilized antibody.

The solid support may be any solid material known to those of ordinary skill in the art to which the antibody may be attached. For example, the solid support may be a test well in a microtiter plate, or a nitrocellulose or other suitable membrane. Alternatively, the support may be a bead or disc formed of glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be bound to, or immobilized on, the solid support using a variety of techniques known to those in the art, which are amply described in the patent and scientific literature. As used herein, the term "bound" refers to both noncovalent association, such as adsorption, and covalent attachment (which may be a direct linkage between the antibody and functional groups on the support or may be a linkage by way of a cross-linking agent). In certain embodiments, binding by adsorption to a well in a microtiter plate or to a membrane is preferred. In such cases, adsorption can be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 μg, and preferably about 100 ng, is sufficient to bind an adequate amount of antibody. Nitrocellulose will bind approximately 100 μg of protein per $cm^3$.

Covalent attachment of the antibody to a solid support may generally be achieved by first reacting the support with a bifunctional reagent that will react with both the support and a functional group, such as a hydroxyl or amino group, on the antibody. For example, the antibody may be bound to supports having an appropriate polymer coating using benzoquinone or by condensation of an aldehyde group on the support with an amine and an active hydrogen on the antibody (see, e.g., Pierce Immunotechnology Catalog and Handbook (1991) at A12-A13).

In certain embodiments, the assay is an enzyme linked immunosorbent assay (ELISA). This assay is performed by first immobilizing an antibody (referred to as the capture antibody) on a solid support, such as the well of a microtiter plate. The immobilized antibody is then incubated with the biological sample, and antigen, such as NS1 (if present in the sample) is allowed to bind to the antibody, to form an antibody-antigen complex or conjugate. The sample may be diluted with a suitable diluent, such as phosphate-buffered saline (PBS) prior to incubation. In general, an appropriate contact time (i.e., incubation time) is that period of time that is sufficient to detect the presence of dengue NS1 protein within a dengue virus-infected sample. Preferably, the contact time is sufficient to achieve a level of binding that is at least 95% of that achieved at equilibrium between bound and unbound antigen. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample can then be removed by washing the solid support with an appropriate buffer, such as PBS containing 0.1% Tween 20™ and detection reagent is added to the solid support. An appropriate detection reagent is any compound that binds to the immobilized antibody-antigen complex and that can be detected by any of a variety of means known to those in the art. Preferably, the detection reagent contains a binding agent (such as, for example, Protein A, Protein G, immunoglobulin, lectin or an antibody) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-antigen complex for an amount of time sufficient to detect the bound antigen. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of NS1 polypeptide in the sample, the signal detected from the reporter group that remains bound to the solid support is generally compared to a signal that corresponds to a predetermined cut-off value. This cut-off value is preferably the average mean signal obtained when the immobilized antibody is incubated with samples from an uninfected patient. In general, a sample generating a signal that is three standard deviations above the mean is considered positive for NS1 and dengue virus infection. In an alternate embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for dengue virus infection.

In one embodiment, the present disclosure provides an ELISA sandwich assay that can be effectively employed to detect the presence of dengue virus infection in a biological sample. In this assay, an antibody specific for a monomeric and/or oligomeric (primarily dimeric) form of NS1 (referred to as the capture antibody) is coated onto ELISA plates. After blocking, the plates are incubated with the biological sample, washed and then incubated with a second antibody specific for a monomeric and/or oligomeric (primarily dimeric) form of NS1 (referred to as the detection antibody), prior to being developed. In one embodiment, the capture antibody is a purified rabbit polyclonal antibody that has been affinity purified against NS1, the detection antibody is a NS1-specific monoclonal antibody disclosed herein, and the plate is developed using a goat anti mouse IgG1 horseradish peroxidase conjugate.

In a second embodiment, the assay is performed in a flow-through or lateral flow format, wherein the anti-NS1 antibody is immobilized on a membrane such as nitrocellulose. In the flow-through test, antigens within the sample bind to the immobilized antibody as the sample passes through the membrane. A detection reagent then binds to the antibody-antigen complex as a solution containing the detection reagent flows through the membrane. The detection of bound detection reagent may then be performed as described above. In the lateral flow format, one end of the membrane to which antibody is bound is immersed in a solution containing the biological sample. The sample migrates along the membrane through a region containing the detection reagent, which preferably includes a colorimetric label, such as colloidal gold, and to the area of immobilized capture antibody. Concentration of detection reagent at the capture antibody indicates the presence of dengue NS1 in the sample. Such tests can typically be performed with a very small amount of biological sample.

FIG. 1 shows an exemplary dipstick which may be employed in the inventive methods to detect the presence of NS1 in a biological sample. In this system, lines are striped (1 μl/cm) on a suitable membrane using an automated biojet system (BioDot, Inc., Irvine, Calif.). The bottom, or test, line 10 consists of a NS1-specific capture antibody in a suitable buffer. One or more test lines can be employed depending on the number of antibodies to be incorporated. The top, or control, line 12 is used as an internal control to make sure that all the test components are working. In this embodiment, control line 12 is protein G or goat anti mouse or rabbit IgG. An anti-NS1 antibody ("detection antibody") conjugated to gold is employed as the detection reagent. Colloidal gold consists of discrete, electron-dense, red-colored particles. When concentrated on solid surfaces, these particles can be visually observed. The detection reagent is dried onto a glass fiber pad, or conjugate pad, 14 and laminated below a membrane. Pads that can be effectively employed as conjugate pad 14 include those available from Whatman Inc. (Florham Park, N.J.), such as the Whatman Rapid Release Pad. A sample pad 16 is soaked in an appropriate buffer, dried and laminated underneath pad 14. Pads that may be effectively employed as sample pad 16 include those available from Ahlstrom Inc. An absorbent top pad 18 is provided to remove excess fluid.

In use, the biological sample is applied onto the end of sample pad 16 and followed with a chase buffer, preferably a phosphate based buffer. The sample mixes with the detection reagent and the resulting complex moves laterally upward and binds to the capture antibody at test line 10 if the sample contains NS1, causing test line 10 to turn red. Unbound complex will continue to travel upwards and will bind to the protein G or goat anti-mouse or rabbit IgG at control line 12 depending on the nature of the antibody chosen for the mobile phase, causing control line 12 to turn red. If a control line is not observed, the test is considered invalid.

Other formats for using the antibodies disclosed herein to detect dengue virus infection in a sample will be apparent to those of ordinary skill in the art. For example, one of skill in the art will appreciate that a mixture of monoclonal antibodies specific for the dengue virus NS1 can be employed in place of a single NS1-specific monoclonal antibody.

The present disclosure also provides kits for use in the diagnosis of dengue virus infection. In certain embodiments, such kits comprise: a dipstick as described above preferably pouched in a generally impermeable container, such as an aluminum foil container, with desiccant; a tube, or vessel, containing lysing buffer; and a disposable transfer pipette for applying solution to the dipstick. In alternative embodiments, such kits comprise: a solid surface, such as a microtiter plate with wells to which a polyclonal antibody specific for the dengue virus NS1 has been immobilized; and a solution containing at least one monoclonal antibody disclosed herein. Such kits can further comprise: at least one control sample selected from the group consisting of: negative controls, positive controls, and cut-off controls; and/or appropriate buffers.

The following Examples are offered by way of illustration and not by way of limitation.

EXAMPLE 1

Preparation of Recombinant NS1 Glycoprotein

Full-length NS1 protein was prepared using a mammalian expression system. Secreted NS1 was concentrated, purified using glass chromatography, and examined by SDS-PAGE under reducing conditions, with and without heat treatment. No heat treatment would ensure that NS1 dimers can be observed by SDS-PAGE. The results demonstrated the presence of glycosylated monomers, glycosylated dimers and a small fraction of non-glycosylated monomers and non-glycosylated dimers.

EXAMPLE 2

Preparation of Antibodies to NS1 Glycoprotein

Polyclonal and monoclonal antibodies against the dengue NS1 glycoprotein isolated as described above were prepared as follows.

30 μg of purified NS1 (prepared as described above) in 50 μl of PBS was emulsified with equal volume of Complete Freund's Adjuvant and injected subcutaneously into a 5 week old female Balb/c mouse. Seven days later, the same amount of NS1 emulsified with Incomplete Freund's Adjuvant was injected intraperitoneally into the same mouse. The injection was repeated once more 21 days after the initial injection. On days 42, 43 and 46, the mouse received intraperitoneal injections of 30 μg of NS1 in 50 μl of PBS without adjuvant. Two days later the animal was sacrificed, and the spleen excised under sterile conditions.

The spleen was homogenized with scissors under serum free RPMI 1640 medium, and passed through a nylon cell strainer to form a splenocyte suspension. Splenocytes were collected by centrifugation, erythrocytes removed by Erythrocyte Lysis Reagent and washed with RPMI 1640. Mouse myeloma cells were grown in H-FSM medium, containing 5% FBS to a density of $4.3\times10^5$/ml. A total number of $5.6\times10^8$ myeloma cells, and separately splenocytes, were washed extensively by centrifugation with RPMI 1640 medium prewarmed to 37° C. The myeloma cells and splenocytes were combined, centrifuged together, and the pellet was gently broken. Cell fusion was performed by adding polyethylene glycol (Mw 1,500) solution dropwise to the cell pellet at 37° C. The resulting cells were washed with RPMI 1640, resuspended in 300 ml of prewarmed H-SFM 5% FBS, and distributed onto thirty 96-well cell culture plates, 100 μl of the cell suspension per well.

The cells were allowed to grow for a day, and were selected with 130 μl per well of the double concentration of HAT medium in H-SFM with FBS. Seven days later, 130 μl of each well content was removed, and replaced with similar, fresh medium, containing HAT at the recommended concentration.

Thirteen days after the cell fusion, culture supernatants of the resulting hybridoma lines were tested by ELISA. NS1 was coated onto ELISA plates (100 ng per well in 50 μl sodium carbonate/bicarbonate buffer pH 9.6) overnight at 4° C., and the wells were blocked with 200 μl per well of 5% nonfat dry milk in PBS containing 0.05% Tween™ 20 (ELISA Wash Buffer, EWB) for 1 hour at room temperature. After blocking, the wells were washed six times with EWB in an automated plate washer, and the hybridoma culture supernatants were incubated in the wells for 1 hour at room temperature. After another wash, the wells were incubated with goat antibodies specific for mouse immunoglobulin, labeled with horseradish peroxidase for 1 hour at room temperature, washed again and visualized with 3,3',5,5'-tetramethylbenzidine reagent. The reaction was stopped with 1N sulfuric acid and read on an ELISA plate reader at 450 nm wavelength.

The hybridoma wells corresponding to positive ELISA results were transferred into wells of a 24-well cell culture plate and grown in 1 ml of H-FSM/FBS medium, containing HT additive. The lines were repeatedly checked for specific antibody secretion by ELISA, expanded, cloned out by limiting dilution and cryopreserved.

The amino acid sequences of the heavy chain variable regions of monoclonal antibodies 528.292, 528.1133 and 528.1299 are provided in SEQ ID NO: 2, 4 and 6, respectively, with the amino acid sequences of the light chain variable regions of monoclonal antibodies 528.292, 528.1133 and 528.1299 being provided in SEQ ID NO: 3, 5 and 7, respectively. Subsequent re-sequencing of the heavy chain variable region of monoclonal antibody 528.1299 gave the sequence of SEQ ID NO: 8.

The ability of the mAbs and rabbit polyclonal antibody to bind to dengue NS1 protein prepared as described above was examined by western blot. Purified NS1 protein samples, either treated or not treated by heat, were analyzed using the mAbs or rabbit polyclonal antibody as the primary antibody. Either the anti-mouse-IgG-HRP or anti-rabbit-IgG-HRP conjugate was appropriately used as the secondary antibody followed by blot development with TMB reagent. The results demonstrated that both NS1 monomers and NS1 dimers (glycosylated and non-glycosylated) are recognized by mAbs 528 292 and 528 1299, and the rabbit polyclonal sera. In contrast, mAb 528 1133 appeared to recognize only the dimeric NS species and/or a heat-sensitive NS1 epitope.

EXAMPLE 3

Characterization of Antibodies Raised Against NS1

Affinity purified rabbit polyclonal antibodies to NS1 were coated onto ELISA plates (100 ng per well in 50 μl sodium carbonate/bicarbonate buffer, pH 9.6) overnight at 4° C. The wells were blocked with 200 μl per well of 5% nonfat dry milk in EWB for 1 hour at room temperature, and washed as above. Cell culture supernatants, containing dengue-1, -2, -3 and -4 serotype NS1 were reacted with plate bound rabbit antibodies, followed by incubation with NS1 specific monoclonal antibodies, and developed with goat antibodies specific for mouse immunoglobulin, labeled with horseradish peroxidase. The ELISA results were visualized as above.

Figure 2:
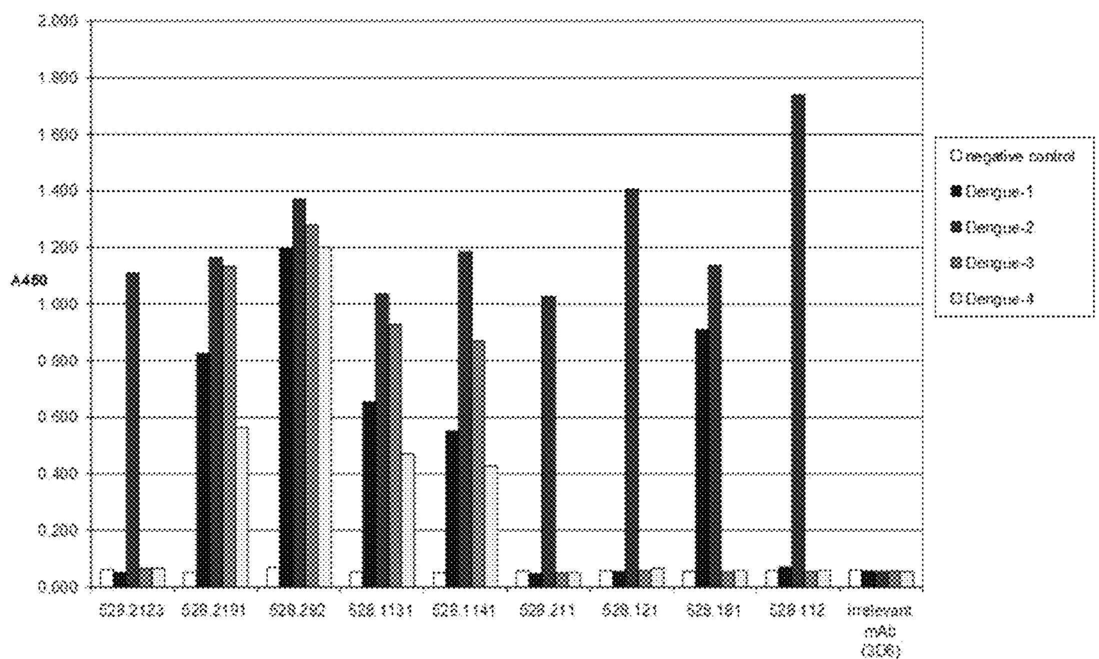
FIG. 2 shows the serotype specificity of dengue-2 NS1-specific monoclonal antibodies of the present disclosure as determined using a sandwich ELISA.

As shown above in FIG. 2, the NS1-specific monoclonal antibodies (mAbs) exhibited at least four classes of specificities: monospecific to dengue-2 (e.g. mAb 528.2123, 528.211, 528.121 and 528.112); all dengue serotype-specific ("pan specific", e.g. mAb 528.292); dengue-1/dengue-2 specific (e.g. mAb 528.181); and mAbs reactive to all dengue serotypes, but with non-uniform reactivity (e.g. 528.1131, 528.2191, 528.1131 or 528.1141; reacting strongest to dengue-2, to a smaller extent to dengue-3, and an even smaller extent to dengue-1 or dengue-4).

Isotypes of dengue-NS1-specific mAbs were evaluated by ELISA, performed on microplates with bound recombinant NS1, as described above. Goat antibodies specific for mouse immunoglobulin were in this case replaced with antibodies specific to single mouse IgG isotypes (IgG1, IgG2a, IgG2b, IgG3, and IgM). Most of the mAbs fall into IgG1 class (see Table 1 below).

TABLE 1

Isotypes of some dengue-2 NS1-specific mAbs

| mAb | Isotype |
|---|---|
| 528.2123 | IgG1 |
| 528.2191 | IgG1 |
| 528.292 | IgG1 |
| 528.1131 | IgG1 |
| 528.1141 | IgG1 |
| 528.211 | IgG1 |
| 528.121 | IgG1 |
| 528.181 | IgG1 |
| 528.112 | IgG2b |

Figure 3:
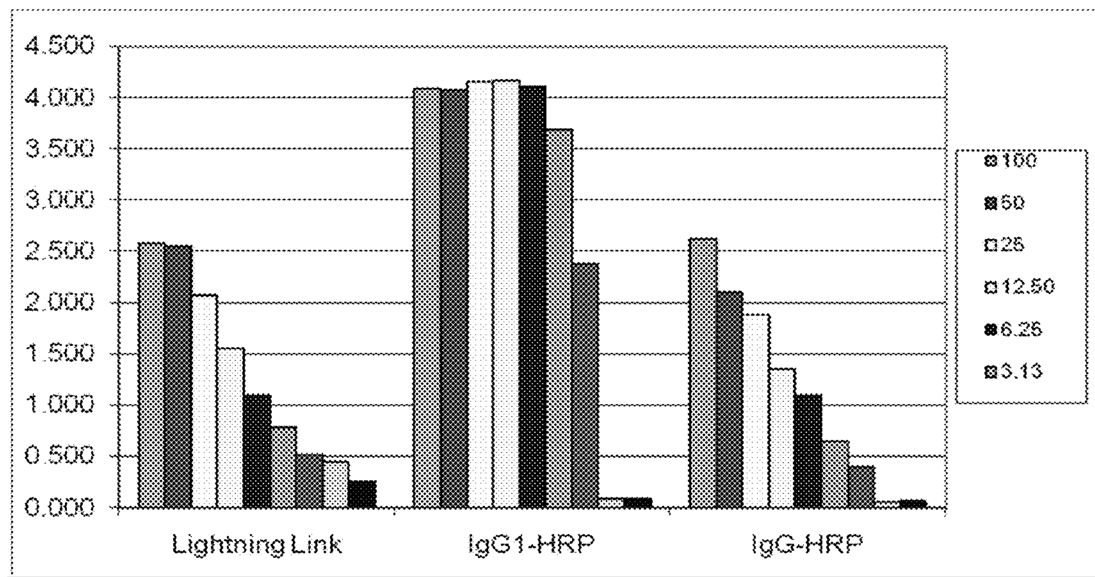
FIG. 3 shows the ability of the pan dengue specific mAb 528.292 in combination with the affinity purified rabbit anti-NS1 polyclonal sera disclosed herein to detect NS1 from all DENV serotypes using three different assay formats.

Further studies were performed using the pan dengue specific mAb 528.292 in combination with the affinity purified rabbit anti-NS1 polyclonal sera to assess its performance in detection of NS1 from all DENV serotypes. Initially three different assay formats were tried: direct linking of mAb with HRP using Lightning Link; (b) using a polyclonal antibody to mouse IgG conjugated to HRP; and (c) using a polyclonal antibody to mouse IgG1 conjugated to HRP. The data are shown in FIG. 3 and show that the use of the anti-mouse IgG conjugate gave the most sensitive assay when tested with NS1 from DENV2.

Figure 4:
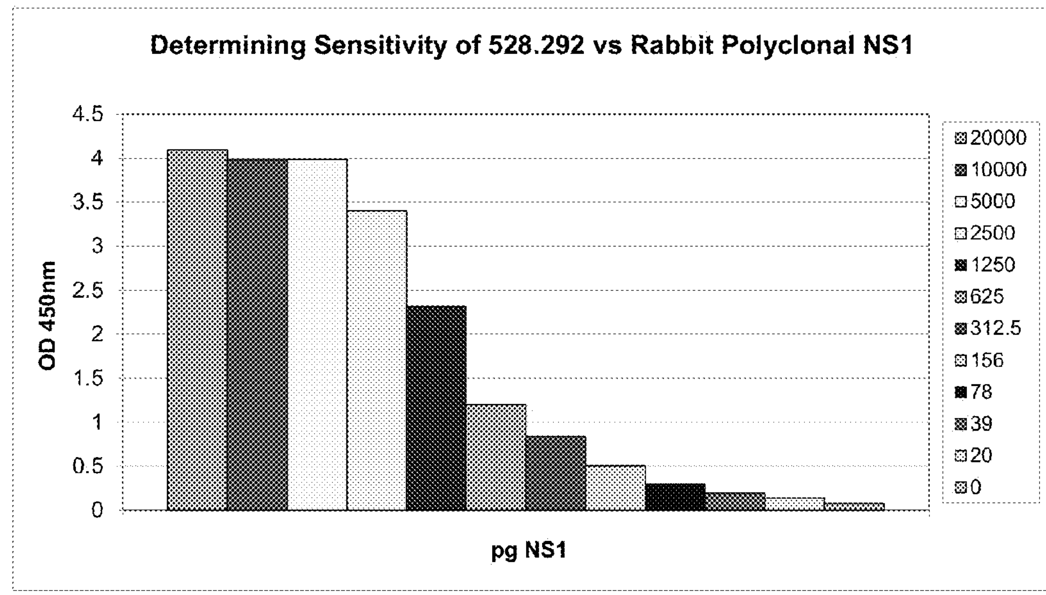
FIG. 4 shows the ability of the pan dengue specific mAb 528.292 in combination with the affinity purified rabbit anti-NS1 polyclonal sera to detect low levels of NS1.
Figure 5:
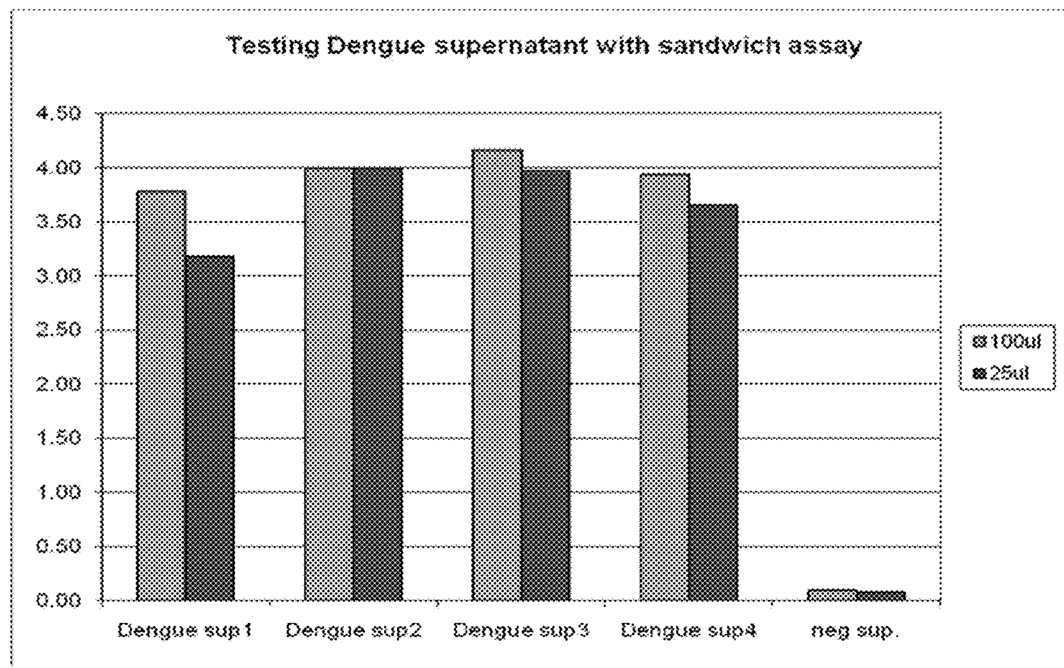
FIG. 5 shows the ability of the pan dengue specific mAb 528.292 in combination with the affinity purified rabbit anti-NS1 polyclonal sera to react with supernatant from the four dengue serotypes.

Closer inspection of the low end sensitivity of this assay indicated that levels of 20 pg were detectable (FIG. 4). The assay was used to detect the reactivity with the supernatants containing the dengue serotypes and all four were shown to be reactive (FIG. 5).

EXAMPLE 4

Epitope Comparison for NS1-Specific Monoclonal Antibody 598.292

Figure 6:
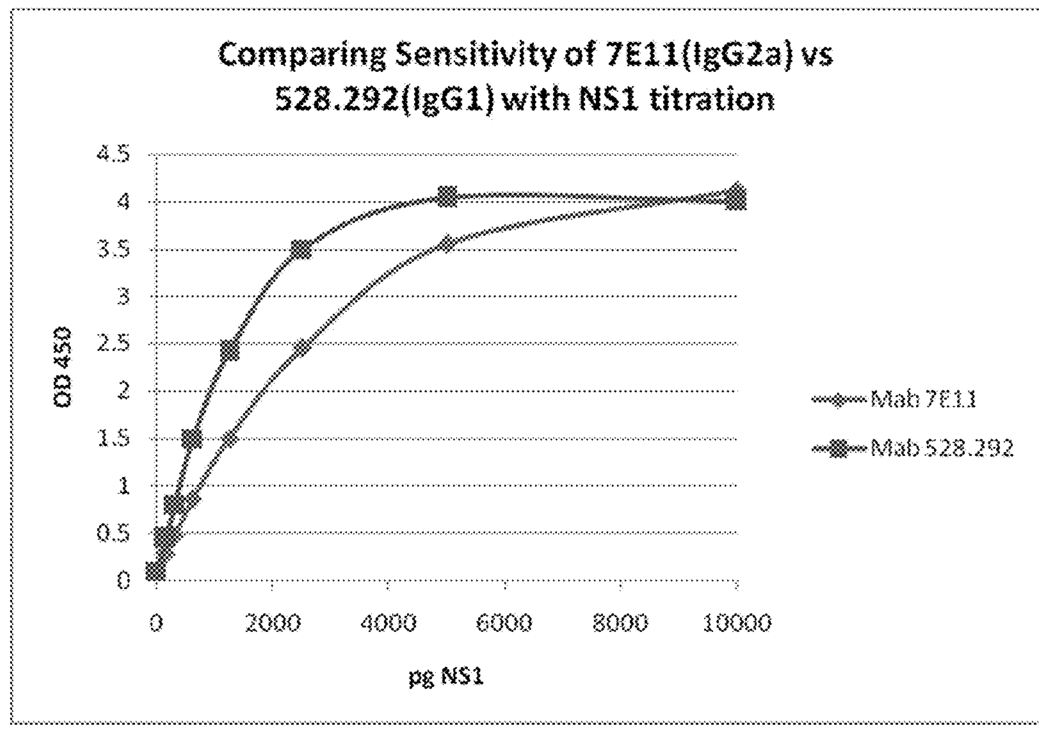
FIG. 6 shows results demonstrating that the mAb 528.292 disclosed herein is approximately 2-3 times more sensitive in a sandwich ELISA assay than the known pan DENV serotype reactive NS1 antibody 7E11.

A pan DENV serotype reactive NS1 antibody (7E11) was obtained that was generated in a different format. This antibody was an IgG2a. It was observed that mAb 598.292 could not sandwich with this one so we anticipated they hit a similar epitope. Initially we optimized both antibodies in a sandwich ELISA with the affinity purified polyclonal anti-NS1 and demonstrated that the sandwich assay using the 528.292 antibody was 2-3 times more sensitive than that using 7E11 (FIG. 6).

Figure 7:
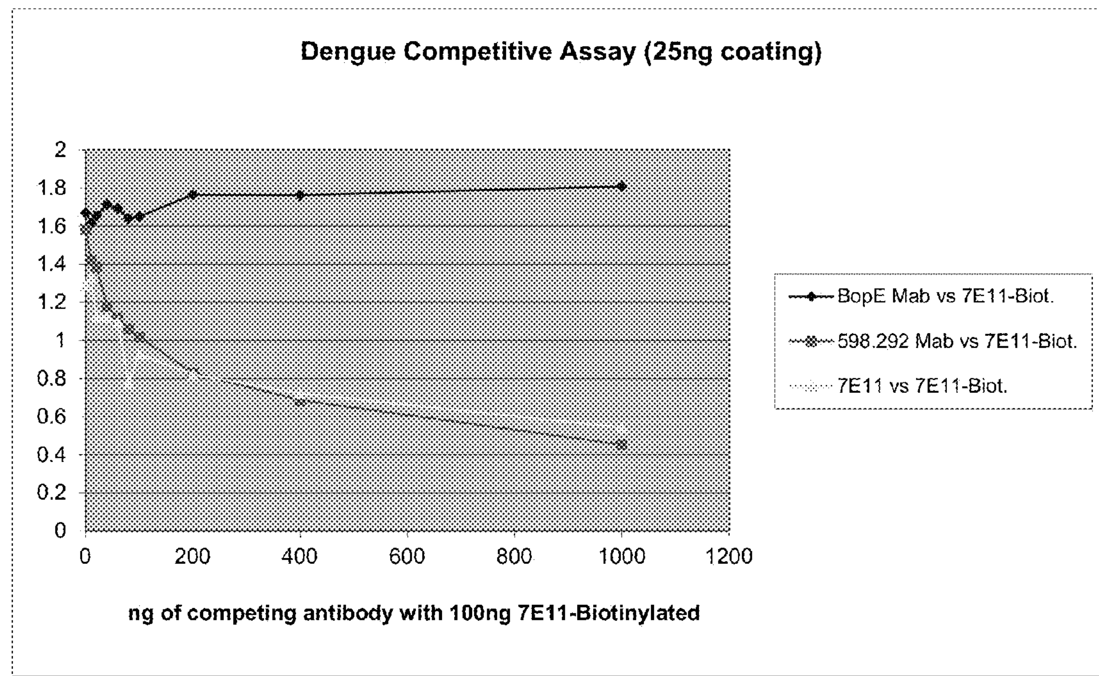
FIG. 7 shows the results of an epitope competition assay using mAb 528.292 and 7E11.

An epitope competition assay was then performed to determine if 7E11 and 528.292 would compete with 7E11 biotinylated in a similar fashion. Plates were coated with 25 ng of NS1 from DENV 2 and then reacted with 7E11 biotinylated in combination with 7E11 unconjugated or 528.292 unconjugated. A monoclonal antibody to BopE, an unrelated protein, was used as a control. As shown in FIG. 7, the inhibition curves were almost identical, indicating that the antibodies are hitting the same epitope.

EXAMPLE 5

Elisa for the Detection of Dengue Virus Infection

A prototype Dengue NS1 sandwich ELISA produced under GMP was evaluated as described below. The ELISA employed a rabbit anti-NS1 capture antibody and three different monoclonal antibodies (528.292, 528.1299 and 528.1133) prepared as described above as secondary reagents. Goat anti-mouse IgG1-HRP was used for the conjugate step. A panel of positive and negative samples was screened using both the Dengue NS1 ELISA and RT-PCR. As shown in Tables 2 and 3 below, the antibodies demonstrated pan dengue serotype NS1 activity More specifically, Dengue virus was cultured in vero cells and serial two-fold titrations of the supernatants of the cultures were evaluated by ELISA using a mixture of mAbs 528.292, 528.1299 and 528.1133 in a 1.6/1.2/1.2 ug/mL dilution. The Dengue NS1 ELISA showed strong reactivity with all four Dengue subtypes in vero culture. This was further confirmed by evaluating the reactivity of the ELISA with serum samples that had been classified as Dengue-1, -2, -3 or -4 using RT-PCR as shown in Table 3.

TABLE 2

Evaluation of Dengue NS1 ELISA with serial dilutions of dengue serotype specific Vero supernatants

| Fold Dilution | Dengue-1 Vero Sup | Dengue-2 Vero Sup | Dengue-3 Vero Sup | Dengue-4 Vero Sup |
|---|---|---|---|---|
| 400X | 3.002 | 3.069 | 3.034 | 3.034 |
| 800X | 2.839 | 2.996 | 2.996 | 2.866 |
| 1600X | 2.889 | 2.932 | 2.781 | 2.227 |
| 3200X | 2.774 | 2.468 | 2.084 | 1.54 |
| 6400X | 2.037 | 1.584 | 1.207 | 0.892 |
| 12800X | 1.228 | 0.966 | 0.708 | 0.574 |
| 25600X | 0.698 | 0.551 | 0.43 | 0.365 |
| 51200X | 0.443 | 0.356 | 0.309 | 0.275 |
| 102400X | 0.25 | 0.228 | 0.186 | 0.174 |
| 204800X | 0.189 | 0.188 | 0.159 | 0.17 |

TABLE 3

Detection of NS1 in patients from all Dengue serotypes

| Sample ID | Day | RT-PCR | Dengue NS1 ELISA Result |
|---|---|---|---|
| RT-PCR characterized samples* | | | |
| S9902929 | 1 | D1(31/29/29) | 1.765 |
| DN9900615A | 5 | D3(32/29/27) | 3.148 |
| DN9900258A | 7 | D3(33/33/40) | 2.869 |
| DN9900497A | 5 | D4(38/35/30) | 2.052 |
| DN9900364A | 7 | F/D(No Ct/No Ct)* | 0.280 |
| S9902959 | 1 | D2(24/20/27) | 0.091 |
| S9903037 | 1 | D2(24/23/26) | 0.128 |
| S10001534 | 2 | D2(31/28/27) | 0.107 |
| S9904911 | 1 | D3(34/30/31) | 0.069 |
| S10001780 | 2 | D4(34/26/29) | 0.450 |
| S9902358 | 2 | D4(35/24/41) | 2.301 |
| DN9900334A | 6 | D4(No Ct/35/31) | 1.239 |
| S10001780B | 8 | ND* | 0.095 |
| CK | 2 | ND* | 3.159 |
| S10000630 | 2 | D1(22/22/23) | 2.786 |
| S9903229 | 1 | D3(27/23/27) | 0.923 |
| 54 | 2 | D4(32/23/19) | 2.096 |
| DN9900436A | 2 | D4(39/33/25) | 0.674 |
| 45 | — | D4(41/33/29) | 1.234 |
| Negative Samples | | | |
| DN10000184A | 3 | — | 0.084 |
| S1002348 | — | — | 0.088 |
| S1002347 | — | — | 0.077 |
| S1002345 | — | — | 0.091 |
| S1002346 | — | — | 0.07 |
| S1002344 | — | — | 0.086 |
| S1002343 | — | — | 0.071 |
| S1002342 | — | — | 0.082 |
| S1002341 | — | — | 0.082 |
| S1002340 | — | — | 0.086 |
| InBios Cut-off | | | 0.105 |

*These samples were also evaluated using Dengue IgM ELISA. The Dengue IgM ratios (Dengue antigen/normal cell antigen) for samples DN9900364A, S10001780B and CK were 19.20 (positive), 5.22 (positive) and 1.17 (negative).

The ELISA was run according to the kit insert. Samples greater than the cut-off sample OD value were considered positive and samples lower than the cut-off sample OD value were considered negative.

From the foregoing, it will be appreciated that, although specific embodiments of the invention have been described herein for the purpose of illustration, various modifications may be made without deviating from the spirit and scope of the invention.

SEQ ID NO: 1-8 are set out in the attached Sequence Listing. The codes for polynucleotide and polypeptide sequences used in the attached Sequence Listing confirm to WIPO Standard ST.25 (1988), Appendix 2.

All references disclosed herein, including patent references and non-patent references, are hereby incorporated by reference in their entirety as if each was incorporated individually.

We claim:

1. A monoclonal antibody, or antigen binding fragment thereof, that is specific for a dengue virus NS1 polypeptide, wherein the monoclonal antibody comprises a heavy chain variable region comprising SEQ ID NO: 4 and a light chain variable region comprising SEQ ID NO: 5.

2. An isolated polynucleotide comprising a nucleic acid that encodes an amino acid sequence selected from the group consisting of: SEQ ID NO: 4 and 5.

3. An isolated host cell comprising the isolated polynucleotide of claim 2.

4. A method for detecting dengue virus infection in a biological sample, comprising:

a. contacting the biological sample with a monoclonal antibody of claim 1 to form a monoclonal antibody-NS1 polypeptide complex; and b. contacting the monoclonal antibody-NS1 polypeptide complex with a detection reagent that binds to the complex, thereby detecting dengue virus infection in the biological sample.

5. A method for detecting dengue virus infection in a biological sample, comprising:

a. contacting the biological sample with a polyclonal antibody specific for a dengue NS1 polypeptide to form a polyclonal antibody-NS1 polypeptide conjugate;

b. contacting the polyclonal antibody-NS1 polypeptide conjugate with a monoclonal antibody of claim 1 to form a polyclonal antibody-NS1 polypeptide-monoclonal antibody conjugate; and c. detecting the presence of the polyclonal antibody-NS1 polypeptide-monoclonal antibody conjugate, thereby detecting dengue virus infection in the biological sample.

6. The method of claim 5, wherein at least one of the monoclonal antibody and the polyclonal antibody is labeled with a detection reagent.

7. The method of claim 6, wherein the detection reagent comprises a reporter group.

8. The method of claim 7, wherein the reporter group is selected from the group consisting of: enzymes, substrates, cofactors, inhibitors, dyes, radionuclides, luminescent groups, fluorescent groups, colorimetric indicators, and biotin.

9. The method of claim 5, wherein the biological sample is selected from the group consisting of: blood, serum, plasma, saliva, cerebrospinal fluid, and urine.

10. The method of claim 5, wherein the polyclonal antibody is immobilized on a solid support.

11. A method for detecting dengue virus infection in a biological sample, comprising:

a. contacting the biological sample with a monoclonal antibody of claim 1 to form a monoclonal antibody-NS1 polypeptide conjugate;

b. contacting the monoclonal antibody-NS1 polypeptide conjugate with a polyclonal antibody specific for a dengue NS1 polypeptide to form a monoclonal antibody-NS1 polypeptide-polyclonal antibody conjugate; and c. detecting the presence of the monoclonal antibody-NS1 polypeptide-polyclonal antibody conjugate, thereby detecting dengue virus infection in the biological sample.

12. The method of claim 11, wherein at least one of the monoclonal antibody and the polyclonal antibody is labeled with a detection reagent.

13. The method of claim 12, wherein the detection reagent comprises a reporter group.

14. The method of claim 13, wherein the reporter group is selected from the group consisting of: enzymes, substrates, cofactors, inhibitors, dyes, radionuclides, luminescent groups, fluorescent groups, colorimetric indicators, and biotin.

15. The method of claim 11 wherein the biological sample is selected from the group consisting of: blood, serum, plasma, saliva, cerebrospinal fluid, and urine.

16. A diagnostic kit for detecting dengue virus infection in a biological sample, comprising:

a. a monoclonal antibody of claim 1; and b. a detection reagent.

17. The kit of claim 16, wherein the detection reagent comprises a reporter group selected from the group consisting of: enzymes, substrates, cofactors, inhibitors, dyes, radionuclides, luminescent groups, fluorescent groups, colorimetric indicators, and biotin.

18. A kit for detecting dengue virus infection in a biological sample, comprising:

a. at least one solid surface on which a polyclonal antibody specific for a dengue NS1 polypeptide is immobilized;

b. at least one control selected from the group consisting of: positive dengue virus controls, negative dengue virus controls and cut-off controls; and c. a solution comprising a monoclonal antibody of claim 1.

19. A dipstick for detecting dengue virus infection in a biological sample, comprising:

a. a lateral flow membrane;

b. a first area positioned at a first, lower, end of the lateral flow membrane for receiving a test sample, wherein the first area comprises a polyclonal antibody specific for a dengue NS1 polypeptide, the polyclonal antibody being labeled with a reporter agent;

c. a second area positioned at a second, upper, end of the lateral flow membrane comprising an immobilized control polypeptide; and d. a third area positioned between the first and second areas, wherein the third area comprises an immobilized monoclonal antibody of claim 1.

20. A kit comprising the dipstick of claim 19.

21. A method for detecting dengue virus infection in a biological sample, comprising:

a. contacting the biological sample with a monoclonal antibody of claim 1 that binds to a nonhexameric form of NS1 to form a monoclonal antibody-NS1 polypeptide complex; and b. contacting the monoclonal antibody-NS1 polypeptide complex with a detection reagent that binds to the complex, thereby detecting dengue virus infection in the biological sample.

* * * * *